United States Patent
Hatch et al.

(10) Patent No.: US 6,918,874 B1
(45) Date of Patent: Jul. 19, 2005

(54) ATTRIBUTE COMPENSATION FOR ANALYTE DETECTION AND/OR CONTINUOUS MONITORING

(75) Inventors: Michael R. Hatch, Sugar Hill, GA (US); Jonathan A. Eppstein, Atlanta, GA (US); Stuart McRae, Atlanta, GA (US)

(73) Assignees: SpectRx, Inc., Norcross, GA (US); Altea Technologies, Inc., Tucker, GA (US)

( * ) Notice: Subject to any disclaimer, the term of this patent is extended or adjusted under 35 U.S.C. 154(b) by 0 days.

(21) Appl. No.: 09/786,830

(22) PCT Filed: Sep. 10, 1999

(86) PCT No.: PCT/US99/20796

§ 371 (c)(1),
(2), (4) Date: May 22, 2001

(87) PCT Pub. No.: WO00/15102

PCT Pub. Date: Mar. 23, 2000

Related U.S. Application Data

(60) Provisional application No. 60/140,285, filed on Jun. 18, 1999, provisional application No. 60/140,283, filed on Jun. 18, 1999, and provisional application No. 60/099,733, filed on Sep. 10, 1998.

(51) Int. Cl.[7] .............................................. A61B 5/00
(52) U.S. Cl. ...................... 600/365; 600/309; 600/347; 600/573; 604/20
(58) Field of Search .............................. 600/365, 309, 600/345, 347, 348, 354, 355, 357, 372, 382, 384, 396, 397, 573, 578; 604/19, 20

(56) References Cited

U.S. PATENT DOCUMENTS

| 5,771,890 A | * | 6/1998 | Tamada | 600/347 |
| 6,023,629 A | * | 2/2000 | Tamada | 600/347 |
| 6,298,254 B2 | * | 10/2001 | Tamada | 600/347 |

FOREIGN PATENT DOCUMENTS

| WO | WO 91/00998 | 1/1991 |
| WO | WO 94/06019 | 3/1994 |
| WO | WO 94 14062 | 6/1994 |
| WO | WO 96/00110 | 1/1996 |
| WO | PCT/US99/20796 | 11/1999 |

* cited by examiner

*Primary Examiner*—Fadi H. Dahbour
(74) *Attorney, Agent, or Firm*—Needle & Rosenberg, PC.

(57) ABSTRACT

A system and method for detecting a measuring an analyte in a biological fluid of an animal. A harvesting device (10) is provided suitable for positioning on the surface of tissue of an animal to harvest biological fluid therefrom. The harvesting device (10) comprises an analyte sensor (50) positioned to be contacted by the harvested biological fluid and which generates a measurement signal representative of the analyte. At least one attribute sensor (40) is provided to measure an attribute associated with the biological fluid harvesting operation of the harvesting device (10) or the assay of the biological fluid, and which generates an attribute signal representative of the attribute. Adjustments are made to operational parameters of the harvesting device (10) based on the one or more attributes.

3 Claims, 5 Drawing Sheets

US 6,918,874 B1

ATTRIBUTE COMPENSATION FOR ANALYTE DETECTION AND/OR CONTINUOUS MONITORING

This application claims priority to U.S. Provisional Application No. 60/099,733 filed Sep. 10, 1998; U.S. Provisional Application No. 60/140,283 filed Jun. 18, 1999 and U.S. Provisional Application No. 60/140,285 filed Jun. 18, 1999.

BACKGROUND OF THE INVENTION

The present invention relates to a system and method for the compensation of assay measurements of analytes from small quantities of biological fluids harvested from tissue of a subject utilizing conditions at the harvesting and assay or measurement site.

Current analyte assay devices suffer from inaccuracies resulting from a variety of confounding conditions at the harvesting site. For example, blood glucose meters adjust an assay measurement for ambient temperature conditions associated with the glucose test strip when it is inserted in the meter.

As attempts are made to reduce the volume of biological fluid collected or the time required for the assay, these conditions become more and more detrimental to an accurate assay measurement. The conditions include, but are not limited to, humidity, temperature, ambient light, pressure, etc. For example, this is particularly the case in a system that measures a glucose concentration from blood or interstitial fluid collected in a harvesting device that is placed in or about the surface of a tissue. Attribute compensation is even more important in a system that monitors an analyte on a continuous basis from a harvesting device that is kept in contact with the tissue for several hours, days or even weeks. Through the use of appropriate sensors, these conditions may be monitored and compensated for in the desired assay measurement.

SUMMARY OF THE INVENTION

In accordance with the present invention, at least one sensor is provided to measure an attribute associated with the biological fluid harvesting operation of a device or the assay of the biological fluid for one or more analytes by the device. A variety of attributes, or conditions, at the harvesting site of the fluid or within the fluid handling portions within the device may affect the accuracy of the assay or other operational parameters of the device. The types of sensors used are based upon the conditions that are measured. An operational parameter of the harvesting device is compensated for (i.e., adjusted) based on the sensed attribute. Examples of attributes are temperature, pH, conditions of the tissue affecting fluid productivity, etc.

The present invention is useful in a system that performs a single (one time) measurement of an analyte in a biological fluid of a subject from a harvesting device placed in contact with the tissue, as well as in a system that continually monitors an analyte from a subject from such a harvesting device. Thus, it is contemplated that an analyte in a biological fluid of a subject may be repeatedly assayed at regular and frequent intervals by the system and method of this invention.

The above and other objects and advantages of the present invention will become more readily apparent when reference is made to the following description, taken in conjunction with the accompanying drawings.

DETAILED DESCRIPTION OF THE INVENTION

Definitions

Figure 1:
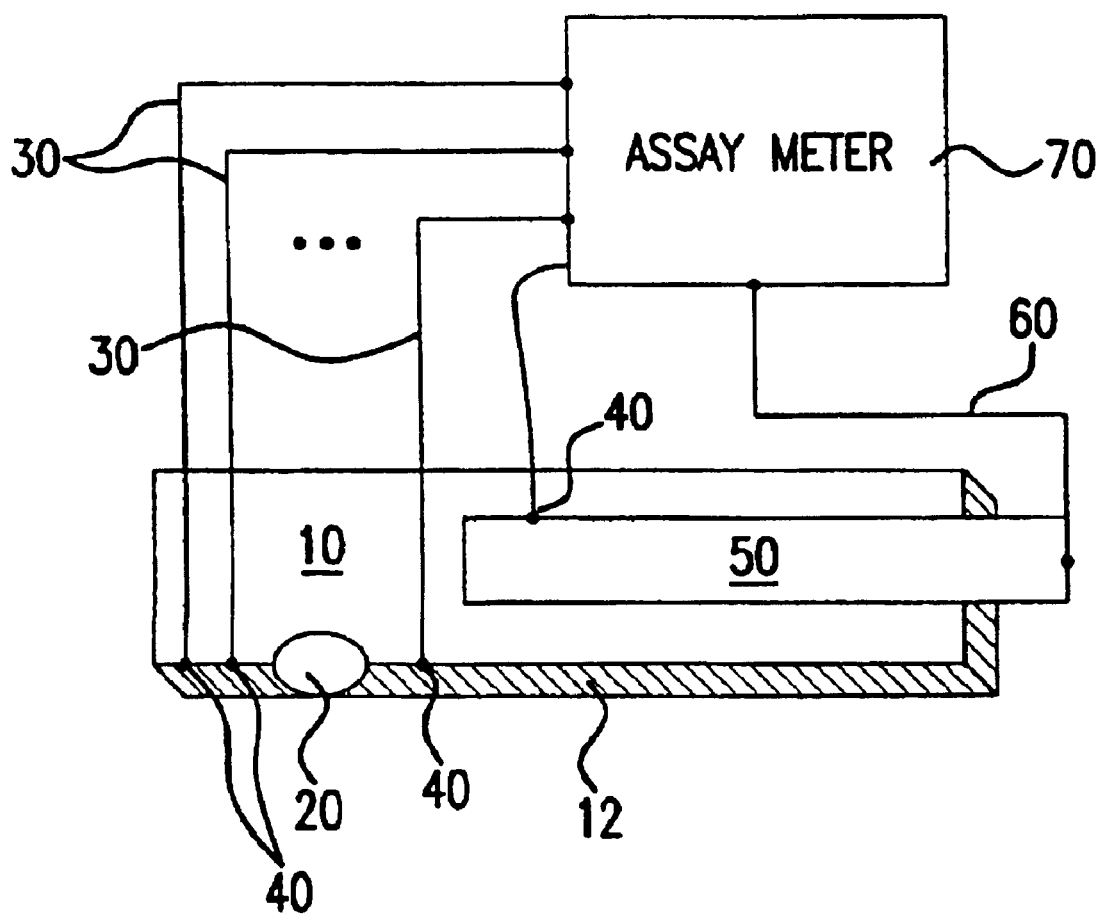
FIG. 1 is a block diagram illustrating a system according to one embodiment of the present invention.

As used in this specification, "a" and "an" may mean one or more than one. For example, "an" analyte may mean one analyte or more than one analyte.

As used herein, the term "biological membrane" means the structure separating one area of an organism from another area of the organism, such as a capillary wall, or the outer layer of an organism which separates the organism from its external environment, such as skin, buccal mucosa or other mucous membrane. The term "epithelial tissue," when used herein is mean to mean skin, mucosa and linings of the body cavities of an organism.

As used herein, the term "tissue" means an aggregate of cells of a particular kind, together with their intercellular substance, that forms a structural material. At least one surface of the tissue is preferably, but not necessarily, accessible to electromagnetic radiation so that one embodiment of the invention can be carried out. The preferred tissue is the skin. Other tissues suitable for use with this invention include mucosal tissue and soft organs.

As used herein, the term "suction" or "pressure" relates to the relative pressure as compared to the internal pressure of the organism to which the system is interfaced. "Vacuum" is used synonymously with the term "suction."

As used herein, the term "biological fluid" means blood serum, whole blood, interstitial fluid, lymph fluid, spinal fluid, plasma cerebrospinal fluid, urine, prostatic fluid, bile, pancreatic secretions, or any combination of these fluids. Other fluids that may be harvested from the surface of various tissues include fluids selected from the group consisting of mucus, saliva, breast milk, tears, gastric secretions and perspiration. "Interstitial fluid" means the clear fluid that occupies the space between the cells in the body. It is also contemplated that biological fluids can be harvested from beneath the surface of tissue of other organs, particularly during operative procedures.

As used herein, "poration," "microporation," or any such similar term means the artificial formation of a small hole, opening or pore to a desired depth in or through a biological membrane, such as skin or mucous membrane, or the outer layer of an organism to lessen the barrier properties of this biological membrane to the passage of biological fluids, such as analytes from within the biological membrane or the passage of permeants or drugs from without the biological membrane into the body for selected purposes, or for certain medical or surgical procedures. The size of the hole or "micropore" so formed is approximately 1–1000μm in diameter. It is to be understood that the term "micropore" is used in the singular form for simplicity, but that multiple openings or pores may be formed by the integrated device according to the present invention.

As used herein, "artificial opening" means any physical breach of the biological membrane of a suitable size for delivering or extraction fluid therethrough, including micropores.

As used herein, the term "harvesting device" means a device suitable for being placed in contact with tissue for collecting a biological fluid sample from the tissue (preferably through the micropores so created) and analyzing the biological fluid to determine a characteristic thereof. The harvesting device may be designed for one time, i.e., discrete use, or may be designed to be placed in contact with the tissue for longer periods of time, e.g., hours, days or weeks, for periodic, continual or continuous analyte monitoring. The harvesting device may optional include a porating element (as defined below) located thereon.

The term "porating element" is meant to include any means of forming a micropore, hole or opening described above, including by thermal ablation, mechanically breaching the tissue by lancet or needle, and other known techniques. An example of a mechanical porating element is disclosed in published OCT application WO 9800193, entitled, "Multiple Mechanical Microporation Of Skin Or Mucosa." Another porating technique suitable for use in connection with this system is disclosed in PCT Application No. PCT/US99/15967 entitled "Controlled Removal Of Biological Membrane By Pyrotechnic Charge For Transmembrane Transport," filed Jul. 14, 1999.

The term "continuously" or "continually" when used in connection with a analyte monitoring system, means acting on an ongoing basis at a frequency or event rate that may vary depending on a particular application of the system. For example, the output of the sensor may be read on a periodic basis, such as every minute, several minutes, hour, several hours, etc. Moreover, at each reading event, the sensor output is optionally sampled multiple times, so as to obtain a plurality of readings relatively close in time, whereby an average or other adjustment of those multiple readings is made for determining a final reading that is displayed or logged.

As used herein, "analyte" means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, and the like.

An "attribute" is a physical condition present at the harvesting site, assay site, or otherwise associated with the operation of the harvesting device. An example of an attribute is temperature. Other attributes or conditions that are useful to be measured are humidity, ambient light, pressure, vacuum, tissue tone, tissue thickness, tissue moisture content, oxygen, pH, etc.

FIG. 1 illustrates one embodiment of a system comprising a harvesting device 10 and an assay meter 70. The harvesting device 10 comprises collects a sample of biological fluid from tissue such as skin, which fluid is collected through an opening 20 on the skin contact side 12. The harvesting device 10 may include incorporated thereon or therein tissue penetrating or porating means, such as a lancet, thermal ablation (optically or electrically heated) such as disclosed in U.S. Pat. No. 5,885,211. See also PCT applications PCT/US99/16378, filed Jul. 20, 1999; PCT/US99/04990, filed Mar. 5, 1999 and PCT/US99/04983, filed Mar. 5, 1999 for variation configurations of a harvesting device that includes optional on-board tissue penetrating or porating elements.

The harvested fluid is moved by vacuum applied over the opening 20 and/or by capillary action, for example, such that the fluid flows through, across, or on the analyte detection strip or sensor 50. The analyte sensor 50 is coupled by an optical or electrical link 60 to the assay meter 70. One or more sensors 40 are positioned in the harvesting device 10 to measure conditions at the harvesting site at the time the biological fluid is harvested. The sensors 40 are coupled by electrical or optical links 30 to the assay meter 70.

The type of sensor depends on the type of attribute or condition(s) measured. As explained above, the attribute may be temperature, humidity, ambient light, pressure, vacuum, tissue conditions indicative of fluid productivity (tissue tone, tissue thickness, and/or tissue moisture content) etc., or any combination thereof. The point of measurement also depends on the type of attribute or condition(s) measured. Proximity to the assay is important for measuring all environmental dependencies of the assay except for those, which are common to the measurement environment such as humidity, pressure or vacuum. For example, in one embodiment, a hose is provided to supply suction or vacuum to the harvesting device to suck fluid from the tissue into the harvesting device and onto the analyte sensor. This hose provides a mechanism to measure environmental parameters along the hose that would be consistent with the environment at the assay such as humidity, pressure and vacuum level. Those environmental dependencies which should be measured near the assay include ambient light, pH and temperature. To correct for assay temperature dependence the temperature measurement point should be as close to the assay as possible within the same housing material but usually not in contact with the sample. The pH of the fluid being measured can be used to compensate for pH effects on the assay and may be changed by the assay process, therefore pH should be measured in the sample just before the assay in the flow channel.

Tissue characteristics such as tone, thickness and moisture content should be measured close to the sample site on similar tissue. For example, if the sample site is on the mid-volar forearm tissue characteristics should be measured on the mid-volar forearm close to the site. Variations in characteristics have been measured between lower mid, and upper volar forearm sites.

Temperature is particularly important when the harvesting device 10 is part of a discrete or continual glucose monitoring system. For example, an attribute sensor 40 that is responsive to temperature is preferably placed as close as possible to the analyte sensor 50 (if not on it) so that the effects of temperature variation on the analyte sensor can be minimized. Many types of temperature sensors are known in the art that are suitable for use in connection with the present invention. Commonly used sensors include forward biased semiconductor diodes, thermistors, thermocouples, Resistance Temperature Detectors (RTDs), radiation thermometers, fiber optic sensors, bead thermocouples and solid state sensors. For this example, a thermistor is used because of its known temperature characteristics, availability and low cost. Preferably, the response time for the temperature sensor is less than 10 seconds per degree Celsius to minimize noise and allow the temperature measured to track the changes at the assay.

Figure 2:
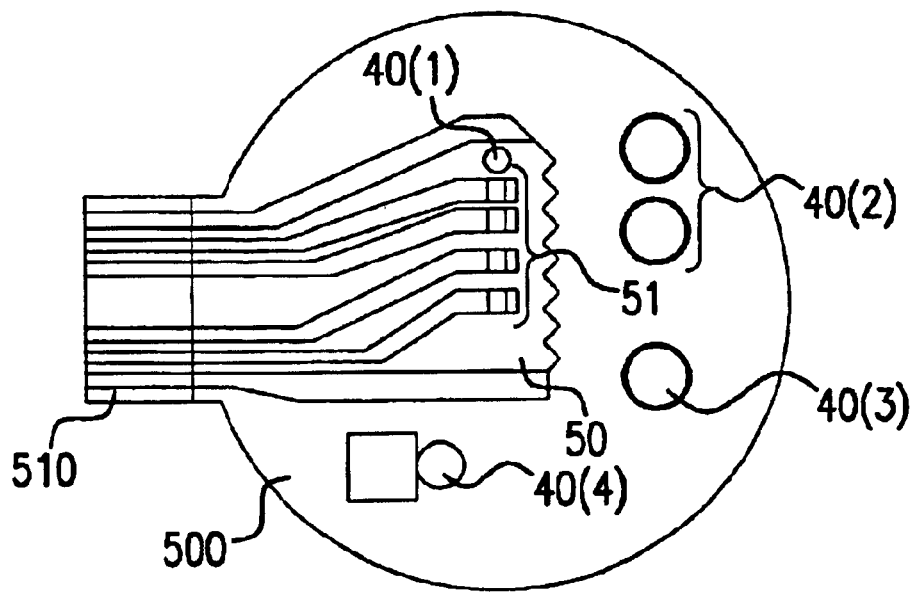
FIG. 2 is a diagram of a sensor head showing the position of attribute sensors according to the invention.
Figure 3:
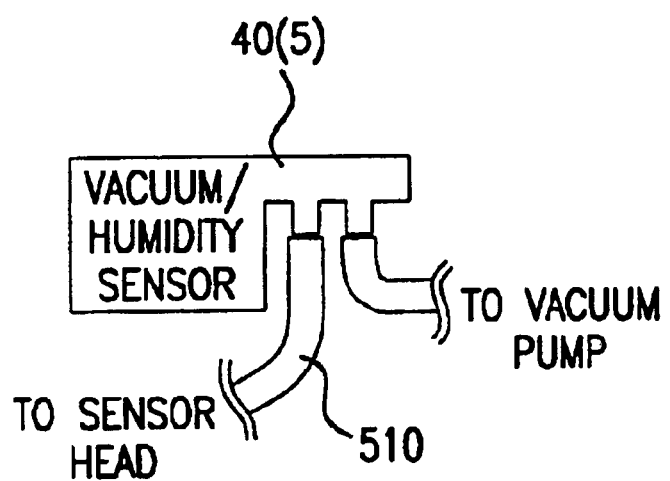
FIG. 3 is a diagram showing the use of a vacuum/pressure sensor according to the invention.

A Turning to FIGS. 2 and 3, an embodiment of sensor head 500 of a harvesting device 10 is shown, wherein the sensor head 500 has one or more attribute sensors positioned thereon. The analyte sensor 50 is, for example, a "primary" sensor for glucose in this application, and can also measure pH or oxygen content in this configuration through working, reference, etc., electrodes 51. Attribute sensor 40(1) is a thermistor placed close to the analyte sensor 50 to measure temperature. Attribute sensor 40(2) is an optical sensor-source pair to profile boundaries in the tissue to which the device 10 is attached, such as skin. Attribute sensor 40(3) measures ambient light, primarily in the ultraviolet (UV) range, where damage to the assay sensor 50 is more common. Attribute sensor 40(4) is a micro-durometer to measure skin conditions or properties, including tone/hardness, which is related to tissue moisture content.

Conditions of the tissue, such as skin, are useful because they indicate the degree of fluid productivity of the tissue. Dry and hard skin produces less fluid than softer skin. If the output of the micro-durometer indicates that the thickness, hardness and/or dryness of the tissue is more than normal, then the amount of suction applied to the harvesting device 10 is increased to ensure sufficient amounts of fluid is extracted. Conversely, if the output of the micro-durometer indicates that the skin is relatively soft, then the vacuum level may be maintained or decreased. This is particularly useful in a continuous monitoring system in which fluid is harvested on a continual basis from a harvesting device located on or about the same harvesting site on the tissue.

As shown in FIG. 3, the sensor head 500 attaches to an assay meter 70 (FIG. 1) by an umbilical cord 510 which carries vacuum and electrical signals. An attribute sensor 40(5) is provided at the meter body which measures pressure and/or vacuum and humidity in the hose inside the umbilical cord 510 that carries vacuum to the sensor head 500.

Figure 4:
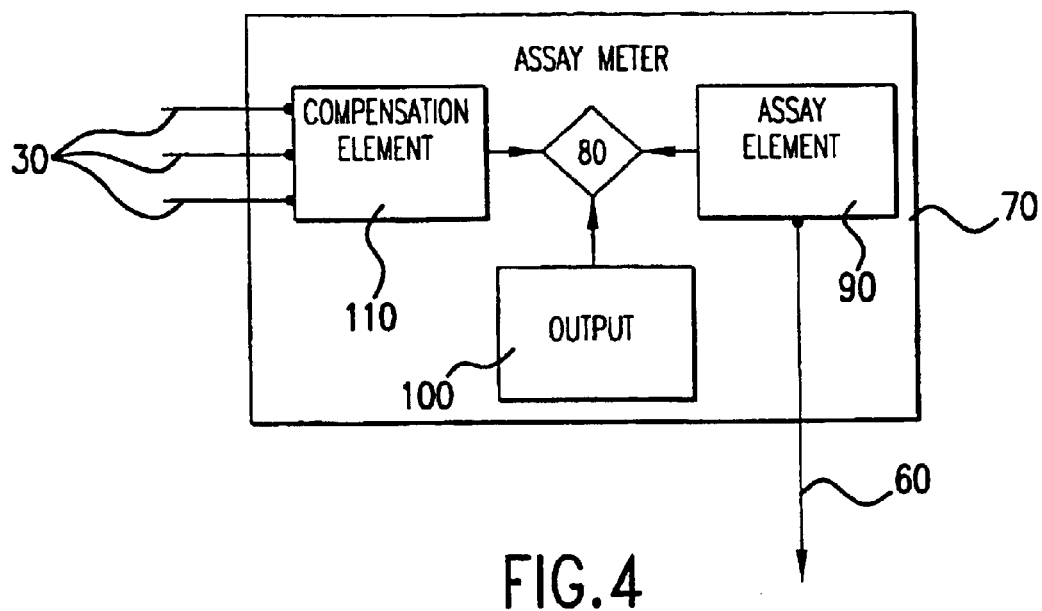
FIG. 4 is a block diagram of the components of an assay meter forming part of the system of FIG. 1.

Referring to FIG. 4, within the assay meter 70 or as a separate component, the attribute signal(s) of the attribute sensor(s) 40 is/are connected to a compensation element 110 which determines the appropriate compensation based upon the attribute signal(s) from the attribute sensor(s) 40. The compensation element 110 generates an appropriate compensation that is output to a processor 80 such as a microprocessor or other computing element. The analyte sensor 50 generates a measurement signal based on the type of analyte being measured. The measurement signal is connected to an assay element 90 within the assay meter 70. The assay element 90 performs a traditional assay of the analyte, generates a signal corresponding to this value and outputs this signal to the processor 80. The processor 80 generates a corrected assay value based upon the compensation signal from the compensation element 110 and the assay signal from the assay element 90 and outputs a signal corresponding to this value to an output means 100 such as a display, a monitoring device or a signal processing device.

The type of compensation to the measurement made by the assay element 90 depends on the conditions sensed at the harvesting site. The compensation applied may be linear or non-linear with respect to the confounding conditions, or utilize a neural network or fuzzy logic. Alternatively, correction may be implemented using a lookup table or an equation-based algorithm. For example, pH effects the efficiency of a glucose oxidase based assay sensor for glucose measurement. If the pH varies, a correction from a lookup table is applied to the assay result to compensate for the variation. Humidity measurements are used in discrete sampling interval systems where the sample is assayed and then is disposed of by the system prior to the next sample being collected. Humidity measurements are also useful in this case to determine if the sample is being collected and humidity differentials are used to quantify change in concentration of the analyte being measured. Humidity measurements are also useful to quantify transepidermal water loss (TEWL). Temperature effects on the efficiency of glucose oxidase based assay are measured and used to generate a lookup table or formula to compensate the assay results for temperature variation. As described above, tissue tone and thickness measurements are useful to estimate the vacuum levels required to maintain sufficient sample flow for proper assay function. As tissue at the site becomes hydrated it will thicken and soften requiring less vacuum for equivalent sample flux.

Figure 5:
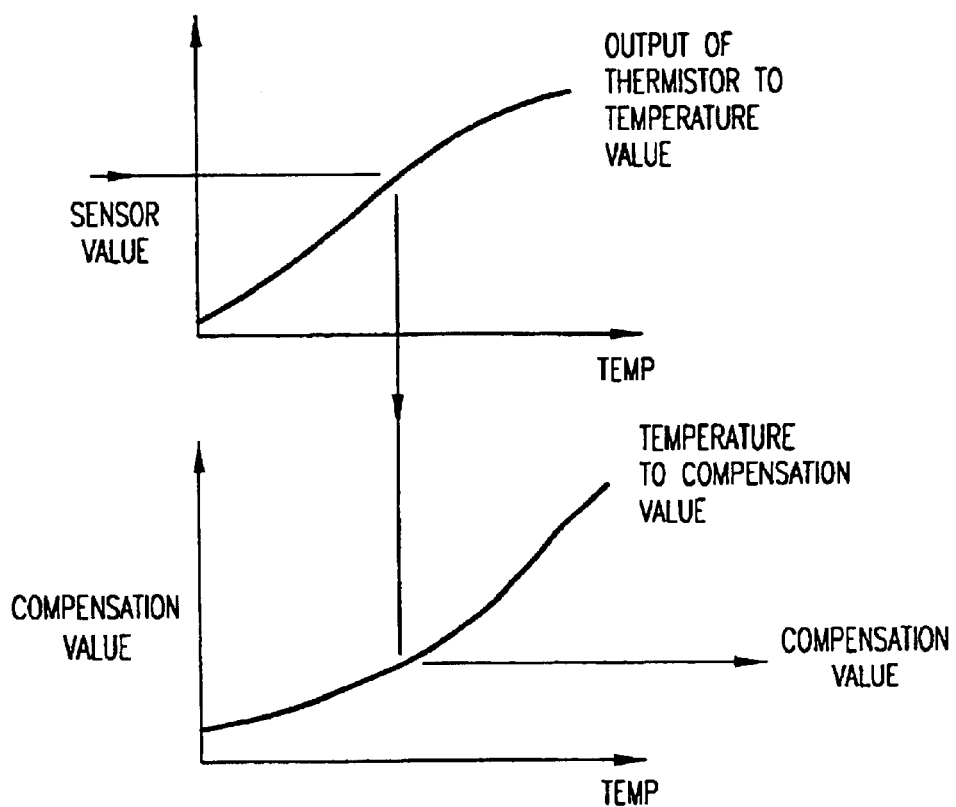
FIG. 5 shows the use of compensation data in graphical form to compensate an assay measurement for temperature.

As an example, FIG. 5 illustrates graphical diagrams that represent the measurement compensation process using temperature measured from a thermistor to compensate a glucose measurement. The upper graph in FIG. 5 shows the conversion from the output of temperature sensor to a temperature value. The lower graph in FIG. 5 shows the compensation factor for a given temperature value derived from the data in the upper graph of FIG. 5. The compensation factor is applied (added or subtracted) to the glucose measurement to improve the accuracy of the glucose measurement. In actual implementation, the conversion process may be implemented in a variety of ways, including a stored lookup table of data representing the graphs shown in FIG. 5. It should be understood that each attribute may involve a compensation process that is similar to that represented by the diagrams of FIG. 5, but with different data. Similarly a multi-dimensioned lookup table may be used to efficiently map the outputs of multiple attribute sensors into a single assay compensation factor.

Figure 6:
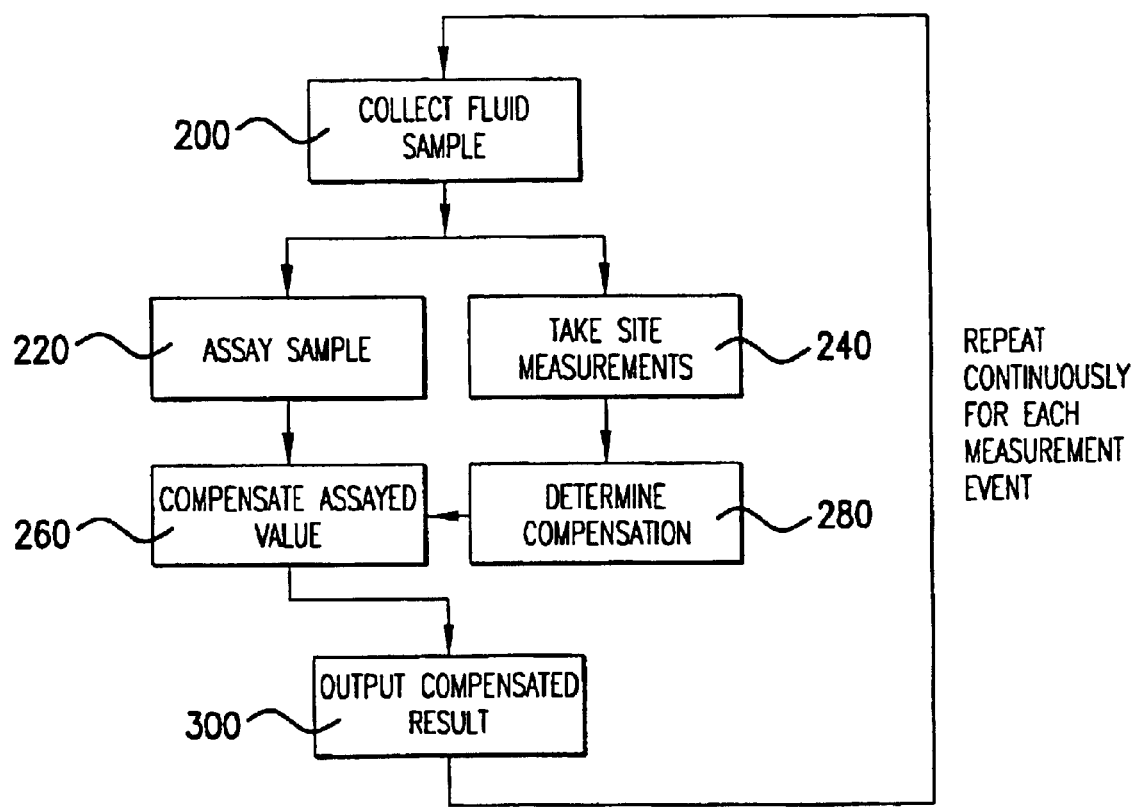
FIG. 6 is a diagram delineating the steps that may be performed by a process according to the present invention.

FIG. 6 shows steps in a process according to the present invention. The first step 200 involves the harvesting of biological fluid for the assay. Step 240 requires the acquisition of condition measurements (i.e., the attributes) relevant to the assay such as temperature, humidity, etc. This step may occur before, during or after step 200. Step 280 determines the assay compensation value from the measured conditions. Step 220 involves the performance of a traditional assay of analyte concentration from the fluid collected in step 200. Step 260 involves the calculation of a corrected assay value by modifying the assay value determined in step 220 with a compensation or adjustment factor determined in step 280. Finally, step 300 outputs the corrected assay measure for subsequent usage such as by a display or processing device.

A particular example of the process of FIG. 6 involves the assay of glucose. Blood or interstitial fluid is harvested through microporation of the harvesting site in step 200. In step 240, the temperature of the analyte sensor 50 is measured. Step 220 assays the harvested interstitial fluid for glucose levels using traditional assay techniques. A compensation factor for the assay based upon the attribute, such as temperature, is made in step 280. The compensated assay value is calculated from the traditional assay measure from step 220 and the compensation measure from step 260. The compensated glucose concentration value is output in step 300.

In a continuous analyte monitoring system, such as that disclosed in PCT application No. PCT/US99/16378 filed Jul. 20, 1999, it is also desirable to compensate for fluctuations in attributes at the harvesting site, in the harvesting device or the analyte sensor, in particular. The process shown in FIG. 6 is repeated on a continual basis. For example, an attribute may be measured continuously, and at each assay or measurement event from the analyte sensor, the attribute signal from the one or more attribute sensors are used to compensate the measurement signal obtained from the analyte sensor.

Figure 7:
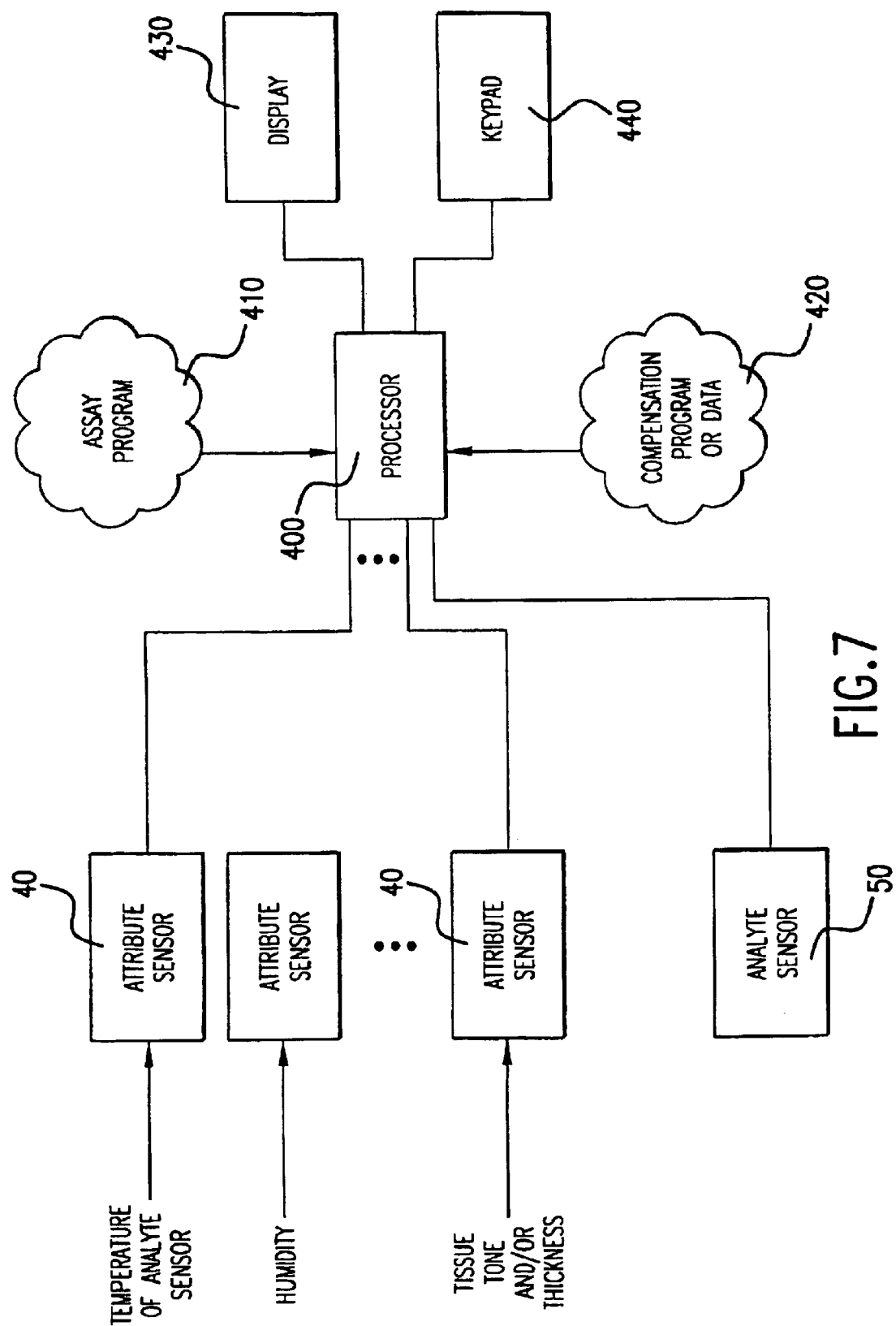
FIG. 7 is a block diagram of a system according to another embodiment of the present invention.

Turning to FIG. 7, another embodiment of the present invention is shown. In this embodiment, a processor 400 performs all of the calculations necessary for deriving a value from the analyte sensor 50, compensated for one or more attributes from one or more attribute sensors 40. For example, the processor 400 is a microprocessor or other programmable processing device that executes an assay program 410 to derive an assay value, compensated for the one or more attributes through the use of a compensation program or data 420. The processor 400 reads a measurement signal from the analyte sensor 50 and one or more attribute signals from the attribute sensors 40, executes the assay program 410 together with the compensation program 420 to obtain a measurement value. The compensation program 420 may be a mathematical algorithm or one or more lookup tables (for each attribute) as described above in conjunction with FIG. 5. This may occur on a discrete or continual basis, depending on the type of environment the system is used. The value generated by the processor 400 may be coupled to a display 430. User interaction with the processor may occur through a keypad 440. The system shown in FIG. 7 may further include memory to store values of attribute signals, particularly in a continual monitoring system, where it is desirable to retain an archive of information.

In summary, the present invention is directed to a system for detecting and measuring an analyte in a biological fluid of a animal, comprising: a harvesting device suitable for positioning on the surface of tissue of an animal to harvest biological fluid therefrom, and comprising an analyte sensor positioned to be contacted by the harvested biological fluid and which generates a measurement signal representative of the analyte; at least one attribute sensor to measure an attribute associated with the operation of the harvesting device and which generates an attribute signal representative of the attribute; and a processor coupled to the attribute sensor and the analyte sensor to receive the attribute signal and the measurement signal, wherein the processor adjusts for an operational parameter of the harvesting device based on attribute signal.

In addition, the present invention is directed to a method for detecting and measuring an analyte in a biological fluid of a subject, comprising steps of: harvesting biological fluid from the surface of tissue of an animal with a harvesting device; contacting an analyte sensor with the biological fluid on the tissue surface; detecting an analyte in the biological fluid with the analyte sensor; sensing an attribute associated with the operation of the harvesting device; and adjusting an operational parameter of the harvesting device based on attribute.

In addition, the present invention is directed to a device suitable for positioning on the surface of tissue of an animal to harvest biological fluid therefrom, and comprising: an analyte sensor positioned to be contacted by the harvested biological fluid and which generates a measurement signal representative of the analyte; and at least one attribute sensor to measure an attribute associated with the operation of the harvesting device and which generates an attribute signal representative of the attribute.

The above description is intended by way of example only and is not intended to limit the present invention in any way except as set forth in the following claims.

What is claimed is:

1. A system for detecting and measuring an analyte in a biological fluid of a animal, comprising:

a harvesting device suitable for positioning on the surface of tissue of an animal to harvest biological fluid therefrom, and comprising an analyte sensor positioned to be contacted by the harvested biological fluid and which generates a measurement signal representative of the analyte;

at least one attribute sensor to measure an attribute associated with the operation of the harvesting device and which generates an attribute signal representative of the attribute, wherein the attribute sensor detects a condition of the tissue indicative of fluid productivity; and a processor coupled to the attribute sensor and the analyte sensor to receive the attribute signal and the measurement signal, wherein the processor adjusts for an operational parameter of the harvesting device based on attribute signal, and wherein the processor generates a signal to control an amount of suction applied to the harvesting device based on the attribute signal.

2. A method for detecting and measuring an analyte in a biological fluid of a subject, comprising steps of:

harvesting biological fluid from the surface of tissue of an animal with a harvesting device;

contacting an analyte sensor with the biological fluid on the tissue surface;

detecting an analyte in the biological fluid with the analyte sensor;

sensing an attribute associated with the operation of the harvesting device, wherein the step of sensing an attribute comprises sensing a condition of the issue indicative of fluid productivity; and adjusting an operational parameter of the harvesting device based on attribute, wherein the step of adjusting comprises adjusting a level of suction applied to the harvesting device for drawing fluid from the tissue into contact with analyte sensor.

3. A method for detecting and measuring an analyte in a biological fluid of a subject, comprising steps of:

harvesting biological fluid from the surface of tissue of an animal with a harvesting device, wherein the step of harvesting comprises continually harvesting biological fluid from the surface of tissue;

contacting an analyte sensor with the biological fluid on the tissue surface;

continually detecting an analyte in the biological fluid with the analyte sensor, wherein the step of detecting an analyte in a biological fluid of a subject comprises continually detecting the analyte;

sensing an attribute associated with the operation of the harvesting device, wherein the step of sensing an attribute comprises continually sensing an attribute proximate to the analyte sensor; and adjusting an operational parameter of the harvesting device based on attribute, wherein the step of adjusting comprises continually adjusting an operational parameter of the device.

* * * * *